US010054575B2

(12) United States Patent
Refai-Ahmed et al.

(10) Patent No.: US 10,054,575 B2
(45) Date of Patent: Aug. 21, 2018

(54) HYDROGEN DETECTOR AND HYDROGEN DETECTION METHOD

(71) Applicant: General Electric Company, Schenectady, NY (US)

(72) Inventors: Gamal Refai-Ahmed, Niskayuna, NY (US); David Peter Robinson, Lisburn (GB)

(73) Assignee: General Electric Company, Schenectady, NY (US)

(*) Notice: Subject to any disclaimer, the term of this patent is extended or adjusted under 35 U.S.C. 154(b) by 250 days.

(21) Appl. No.: 14/866,605

(22) Filed: Sep. 25, 2015

(65) Prior Publication Data
US 2017/0089874 A1    Mar. 30, 2017

(51) Int. Cl.
*G01N 33/00*    (2006.01)

(52) U.S. Cl.
CPC ....... *G01N 33/005* (2013.01); *G01N 33/0009* (2013.01); *G01N 33/0016* (2013.01); *G01N 33/0059* (2013.01); *G01N 33/0014* (2013.01)

(58) Field of Classification Search
CPC ............. G01N 33/005; G01N 33/0014; G01N 33/0016; G01N 33/0009; G01N 33/0059
See application file for complete search history.

(56) References Cited

U.S. PATENT DOCUMENTS

| | | | |
|---|---|---|---|
| 4,397,888 A | 8/1983 | Yannopoulos et al. | |
| 5,879,631 A | 3/1999 | Wewers et al. | |
| 6,277,329 B1 * | 8/2001 | Evans | G01N 33/0013 422/80 |
| 6,464,938 B1 * | 10/2002 | Rongier | G01N 25/32 422/51 |
| 8,025,843 B2 | 9/2011 | Ono et al. | |
| 2005/0090018 A1 | 4/2005 | Walte et al. | |
| 2007/0269346 A1 * | 11/2007 | Wohltjen | G01N 33/0014 422/83 |
| 2013/0034465 A1 * | 2/2013 | Kanno | B60L 3/0053 422/51 |
| 2016/0103082 A1 * | 4/2016 | Kimura | G01N 33/005 73/25.01 |

FOREIGN PATENT DOCUMENTS

EP    1103807 B1    5/2001

OTHER PUBLICATIONS

European Search Report and Opinion issued in connection with corresponding EP Application No. 6190172.3 dated Mar. 1, 2017.

* cited by examiner

*Primary Examiner* — Blake A Tankersley
(74) *Attorney, Agent, or Firm* — Parks IP Law LLC

(57) ABSTRACT

There are provided methods and devices for sensing hydrogen gas. For example, there is provided a method that includes drawing a sample into a channel. The method includes passing the sample over a collection plate to remove an extraneous gas in the sample, thus yielding a purified sample. The method further includes passing the purified sample on a sensing plate and measuring a concentration of hydrogen in the purified sample using the sensing plate. The measuring can include heating the sensing plate and correlating a change in resistance of the sensing plate with a specified concentration of hydrogen. Furthermore, the method can include regenerating the collection plate following the measuring.

20 Claims, 3 Drawing Sheets

100

200

200

300

HYDROGEN DETECTOR AND HYDROGEN DETECTION METHOD

TECHNICAL FIELD

The present disclosure generally relates to hydrogen detection. More particularly, the present disclosure relates to a hydrogen detector and a hydrogen detection method.

BACKGROUND

Conventional hydrogen ($H_2$) gas sensors suffer from poor sensitivity due to the lack of selectivity in their sensing mechanism. Specifically, hydrogen sensors are prone to contamination from carbon monoxide, carbon dioxide, and acetylene, as well as other hydro-carbons, all of which can contribute to an erroneous estimation of the concentration of hydrogen gas in a sample.

In a measurement setting, this cross-contamination can be characterized by a shift from an $H_2$ baseline. Furthermore, in addition to the presence of these contaminants, variations within the sensing layer structure of the sensor as well as the different spatial thermal gradients that arise in the sample prior to measurement also contribute to the shift from the $H_2$ baseline, thereby yielding an incorrect estimation of the hydrogen content. These issues, whether taken alone or together, all contribute in raising the detection limit of current hydrogen sensors.

SUMMARY

The embodiments featured herein help solve or mitigate the above-noted issues as well as other issues known in the art. Specifically, the embodiments provide means for removing contaminants in a sample prior to measurement. Further, the embodiments, provide means for constraining the sample volume during the measurement in order to limit spatial thermal gradients. Furthermore, the embodiments provide means for preventing further generation of trace gases, by conversion from longer hydro-carbons (i.e. methane and ethane), when oil mists are present in the sample, thereby allowing a lower detection limit for hydrogen, relative to conventional sensors.

In one embodiment, there is provided a method that includes drawing a sample into a channel. The method includes passing the sample over a collection plate to remove an extraneous gas in the sample, thus yielding a purified sample. The method further includes passing the purified sample on a sensing plate and measuring a concentration of hydrogen in the purified sample using the sensing plate. The measuring can include heating the sensing plate and correlating a change in resistance of the sensing plate with a specified concentration of hydrogen. Furthermore, the method can include regenerating the collection plate following the measuring.

In another embodiment, there is provided a device that includes a channel, a collection plate, and a sensing plate insulated from the collection plate. The device is configured to measure a concentration of hydrogen adsorbed onto the sensing plate. Further, the device is configured to correlate a change in resistance of the sensing plate with a specified concentration of hydrogen.

In yet another embodiment, there is provided a hydrogen sensor including a sensing plate configured to capture hydrogen in a sample. The hydrogen sensor further includes a regenerative collection plate configured to capture extraneous gaseous elements from the sample, prior to capturing hydrogen at the sensing plate.

Additional features, modes of operations, advantages, and other aspects of various embodiments are described below with reference to the accompanying drawings. It is noted that the present disclosure is not limited to the specific embodiments described herein. These embodiments are presented for illustrative purposes only. Additional embodiments, or modifications of the embodiments disclosed, will be readily apparent to persons skilled in the relevant art(s) based on the teachings provided.

BRIEF DESCRIPTION OF THE DRAWINGS

Illustrative embodiments may take form in various components and arrangements of components. Illustrative embodiments are shown in the accompanying drawings, throughout which like reference numerals may indicate corresponding or similar parts in the various drawings. The drawings are only for purposes of illustrating the embodiments and are not to be construed as limiting the disclosure. Given the following enabling description of the drawings, the novel aspects of the present disclosure should become evident to a person of ordinary skill in the relevant art(s).

DETAILED DESCRIPTION

While the illustrative embodiments are described herein for particular applications, it should be understood that the present disclosure is not limited thereto. Those skilled in the art and with access to the teachings provided herein will recognize additional applications, modifications, and embodiments within the scope thereof and additional fields in which the present disclosure would be of significant utility.

Figure 1:
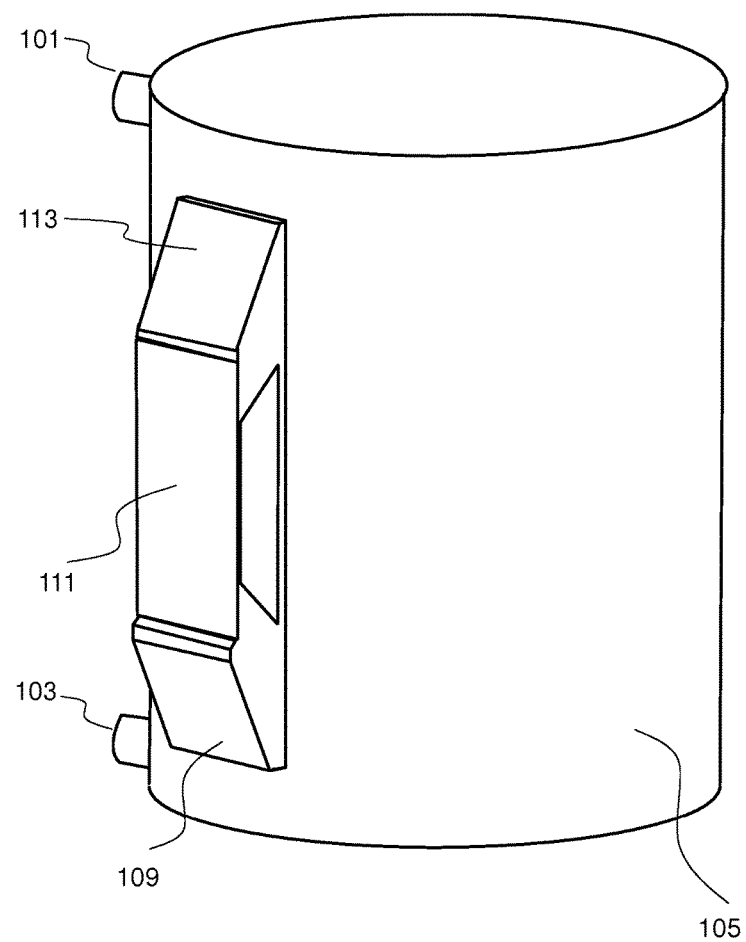
FIG. 1 is an illustration of a device, according to an embodiment.

FIG. 1 is an illustration of a device 100 according to an embodiment. Device 100 can be a hydrogen detector or sensor configured for hydrogen detection. Device 100 can include chamber 105. Chamber 105 includes an inlet 101 and an outlet 103. It is noted that outlet 103 can serve as an inlet and that inlet 101 can serve as an outlet, depending on the configuration. Furthermore, device 100 includes a portion dedicated for purification and analysis of a sample that is introduced, i.e. drawn, into chamber 105. In FIG. 1, this portion is shown as a protuberance on the side of chamber 105 of the channel, and it includes collection plates 109 and 113 and sensing plate 111. Purification and analysis are achieved in the inner surfaces of the portion shown in FIG. 1.

In one embodiment, collection plates 109 and 113 can be made of a material that is inherently configured to absorb specific contaminants typically encountered in hydrogen detection applications. For example, when the sample is air, these contaminants can be carbon monoxide, carbon dioxide, and/or acetylene. As such, collection plates 109 and 113 can be made of silver oxide ($Ag_2O$), which can absorb these contaminants, particularly carbon dioxide. Once the contaminants are removed from the sample, the sample is purified, and it then flows on to sensing plate 111, which can then sense the hydrogen content with no cross-contamination by the extraneous gases originally found in the sample.

One of ordinary skill in the art will readily appreciate that in some embodiments, the collection plates may not remove the entirety of the contaminants in the sample. Nevertheless, in these embodiments, a much reduced concentration of contaminants in the sample during sensing will contribute in lowering the detection limit of hydrogen gas.

Collection plates 113 and 111 are regenerative. That is, once they are saturated with contaminants, they can be made free of the contaminants simply by heating the plates to release the contaminants in gas form from the plates. This can be done using a heater (not shown), which can be controlled using a conventional controller. Typically, in the case of silver oxide, the collection plates can be heated to exceed about 220 degrees Celsius in order to achieve regeneration.

Sensing plate 111 is the element that is used to detect the presence of hydrogen gas in the purified sample. Sensing plate 111 can be made of (or it can include) a tin oxide layer which changes in resistance in response to hydrogen uptake. Upon release of hydrogen from the tin oxide layer, it can return to its original resistance. In a typical measurement scheme using device 100, sensing plate 111 is heated between about 400 degrees Celsius and about 500 degrees Celsius to make the measurements. This may be done with a heater (not shown) controlled using a conventional temperature controller.

Once sensing plate 111 is heated to the above-mentioned temperature range, changes in resistance registered at sensing plate 111 can be correlated with hydrogen concentration using a predetermined concentration vs. resistance calibration curve or calibration table. Further, the resistance of sensing plate 111 can be monitored using a pair of electrodes each placed at a different location of sensing plate 111. In some embodiments, a four-point probe measurement of resistance can be employed using four electrodes; this configuration minimizes the effect of the resistance of the electrodes on the measurement, thereby providing more accurate results than in the two-electrode configuration. Further, it is noted that the present disclosure is not limited to tin oxide as being the sensing material; any hydrogen-sensitive material known in the art is contemplated.

Figure 2A:
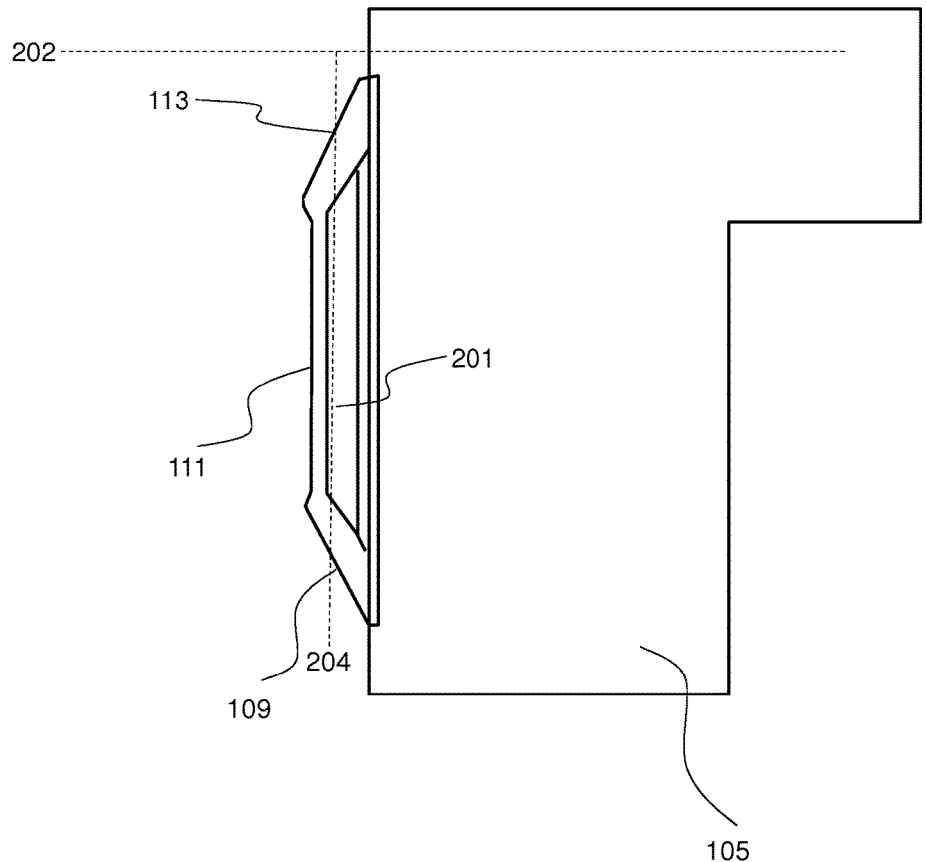
FIG. 2A is a cross-sectional view of a device, according to an embodiment.

Further, in a measurement scheme using device 100, a sample is drawn into chamber 105. The path undertaken by the sample can be thought of as a channel, which has a T-section (see lines 202 and 204 in FIG. 2A illustrating the path of the sample into chamber 105). The channel is insulated in order to limit the internal air volume that is subject to the high temperatures necessary for measurement. If no insulation is provided, the high temperatures required to make the measurement (400 degrees Celsius to 500 degrees Celsius) can cause thermal gradients at sensing plate 111, which would also corrupt the measurement results. In device 100, an insulation material is also used between sensing plate 111 and collection plates 109 and 113. After making the measurement at sensing plate 111, collection plates 109 and 113 can be regenerated as mentioned above. Sensing plate 111 is also allowed to cool to limit the possibility of contaminants freed from collection plates 113 and 109 during regeneration to adsorb onto its surface.

The cross-section at sensing plate 111 also looks like a 'T'. This cross-section forms a sensing channel. (See the dashed lines in FIG. 2A, which is a cross-sectional view of the sensing channel at sensing plate 111). This configuration encourages a larger air flow, due to thermal convection currents. If it was only a thin gap, at sensing plate 111, the surface friction of the thin channel would limit the maximum airflow, but by using a T-Section, this encourages faster flow, while still having a constrained thermal region around the sensor element.

Figure 2B:
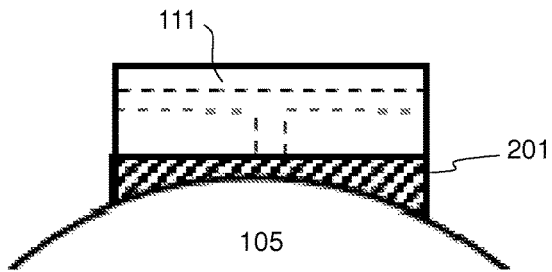
FIG. 2B is a cross-sectional view of a sensing element of the device of FIG. 2A, according to an embodiment.

As shown in FIG. 2, the analysis and purification are both confined to a specified region of the channel, i.e. in the protrusion located on the side of chamber 105. In other words, portions of the sample that are flowing in chamber 105 will not be heated to high temperatures since the analysis and the purification steps are constrained to a much smaller volume located in the protrusion on the side of chamber 105. This configuration prevents the conversion of excessive amounts of lower length hydro-carbons (such as methane and ethane) that can contaminate sensing plate 111 and lead to erroneous measurement results.

Constraining the volume and providing additional insulation is further achieved by a gap 201 between the sensing plate 111 and the body of chamber 105. In some embodiments, gap 201 may be an air gap, whereas in other embodiments it may include an insulation material.

Figure 3:
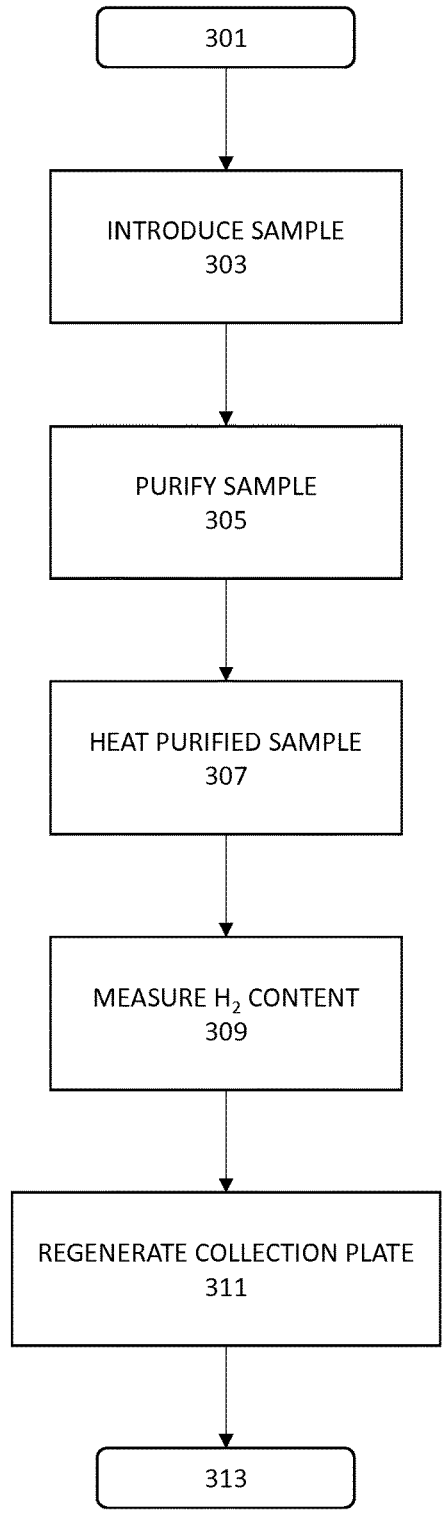
FIG. 3 depicts a flow chart of a method, according to an embodiment.

FIG. 3 depicts a flow chart of an exemplary method 300, according to an embodiment. Method 300 can be executed by a system comprising one or more devices such as device 100. Method 300 begins at block 301. While block 301 is described herein as a "beginning step," one of ordinary skill in the art will readily recognize that block 301 can generally be a transition point in a flow diagram. In other words, block 301 can be a point at which another method ends or it may mark the end of a series of steps similar to those described below in the context of method 300.

Method 300 includes a step 303 in which a sample is introduced in a channel of a hydrogen sensor configured according to the teachings provided in the present disclosure. The sample can be introduced into the channel using conventional means, such as by pumping, thermal convection or merely by diffusion.

Once the sample is introduced in the channel, the sample is purified at a collection plate (step 305). Purification can include removing one more contaminants from the sample. For example, purification can include removing one of carbon dioxide, carbon monoxide, and acetylene. Purification can also include removing at least two of the aforementioned gases in the sample. Furthermore, purification can include, generally speaking, removing hydro-carbons, such as methane and ethane. As mentioned above when discussing exemplary embodiments of the hydrogen sensor, purification can be accomplished at a collection plate. The collection plate can include silver oxide or any other compound that can absorb specific contaminants dictated by the application at hand.

Method 300 can include a step 307 wherein the purified sample is heated between about 400 degrees Celsius and 500 degrees Celsius. Method 300 can also include a step 309 wherein the heated purified sample is made to adsorb over a sensing plate to perform a measurement of the hydrogen content in the purified sample. The measurement can include comparing a change in resistance or a simply comparing a resistance value of the sensing plate with a calibrated resistance value in order to correlate the instant measurement with a known hydrogen gas concentration. One of skill in the art will readily appreciate that step 309 can include any operation that is typical in the measurement and instrumentation arts, namely data filtering, averaging, etc.

Furthermore, method 300 can include a regeneration step 311 wherein once the hydrogen content in the purified sample has been measured and/or estimated, the collection plate can be regenerated to remove the contaminants that adsorbed thereto. This can be done by heating the collection plate to a higher temperature (i.e. for silver oxide >200 degrees Celsius). Doing so frees the collection plate from the contaminants and makes it ready for a subsequent measurement cycle that includes all the steps described above. Furthermore, while regeneration is being achieved on the collection plate, the sensing plate is allowed to cool in order to prevent any uptake of the contaminants at the sensing plate. Method 300 can end at step 313. Generally speaking, however, step 313 can be a transition point, and method 300 can start over at step 301 from step 313. Lastly, it is noted that method 300 can be implemented partially or in whole, without departing from the scope of the teachings disclosed herein.

Those skilled in the relevant art(s) will appreciate that various adaptations and modifications of the embodiments described above can be configured without departing from the scope and spirit of the disclosure. Therefore, it is to be understood that, within the scope of the appended claims, the disclosure may be practiced other than as specifically described herein.

What is claimed is:

1. A device, comprising:
   a chamber; and
   a hydrogen sensor, comprising:
      a sensing channel that provides a path from the chamber through the hydrogen sensor;
      a collection plate, wherein the collection plate is positioned along the path and configured to remove a contaminant from a sample passing through the sensing channel;
      a sensing plate insulated from the collection plate, wherein the sensing plate is positioned along the path downstream of the collection plate, wherein the sensing plate is configured to adsorb hydrogen and change in resistance in response to adsorbing hydrogen;
      a first heater configured to heat the sensing plate; and
      a first temperature controller configured to control the first heater.

2. The device of claim 1, wherein the sensing channel has a T-shaped cross-section.

3. The device of claim 1, wherein a volume of the sensing channel is smaller than a volume of the chamber.

4. The device of claim 1, wherein the collection plate includes a second temperature controller and a second heater.

5. The device of claim 4, wherein the collection plate includes silver oxide.

6. The device of claim 5, wherein the second heater is configured to raise a temperature of the collection plate above 200 degrees Celsius.

7. The device of claim 4, wherein the first temperature controller is configured to heat the sensing plate during a measurement.

8. The device of claim 7, wherein the second temperature controller is configured to heat the collection plate after a measurement to regenerate the collection plate.

9. The device of claim 8, wherein the first temperature controller is configured to allow the sensing plate to cool while the second temperature controller heats the collection plate.

10. The device of claim 1, wherein the first heater is configured to raise a temperature of the collection plate above 400 degrees Celsius.

11. The device of claim 10, wherein the sensing plate includes tin oxide.

12. The device of claim 1, wherein the device is configured to correlate a change in resistance of the sensing plate with a specified hydrogen concentration.

13. The device of claim 12, comprising electrodes to measure a change in resistance of the sensing plate.

14. The device of claim 1, wherein the collection plate includes silver oxide.

15. The device of claim 1, wherein the sensing plate includes tin oxide.

16. The device of claim 1, comprising electrodes to measure a change in resistance of the sensing plate.

17. The device of claim 1, wherein the chamber is insulated from the sensing plate.

18. The device of claim 1, wherein the sample is air.

19. The device of claim 18, wherein the contaminant includes at least one of carbon monoxide, carbon dioxide, and acetylene.

20. A device, comprising:
   a sensing channel that is configured to provide a path from a chamber;
   a collection plate, wherein the collection plate is positioned along the path and configured to remove a contaminant from a sample passing through the sensing channel;
   a sensing plate insulated from the collection plate, wherein the sensing plate is positioned along the path downstream of the collection plate, wherein the sensing plate is configured to adsorb hydrogen and change in resistance in response to adsorbing hydrogen;
   a first heater configured to heat the sensing plate; and
   a first temperature controller configured to control the first heater.

* * * * *